US006676650B1

(12) United States Patent
Magovern et al.

(10) Patent No.: US 6,676,650 B1
(45) Date of Patent: Jan. 13, 2004

(54) PERFUSION CANNULA, METHOD AND SYSTEM

(75) Inventors: James A. Magovern, Pittsburgh, PA (US); Wayne P. Griffin, Cranberry, PA (US); Richard Davis, Grand Rapids, MI (US)

(73) Assignee: CardiacAssist, Inc., Pittsburgh, PA (US)

(*) Notice: Subject to any disclaimer, the term of this patent is extended or adjusted under 35 U.S.C. 154(b) by 0 days.

(21) Appl. No.: 09/400,800

(22) Filed: Sep. 22, 1999

(51) Int. Cl.$^7$ .................. A61M 31/00; A61M 29/00; A61M 37/00
(52) U.S. Cl. .............. 604/508; 604/103.03; 604/102.01
(58) Field of Search ............. 604/93.01, 103.03, 604/103.08, 264, 268, 506–510, 27–28, 30, 48, 500, 96.01, 102.01, 104–109, 131, 164.04, 151–155, 523, 532, 541–544; 606/191, 194

(56) References Cited

U.S. PATENT DOCUMENTS 5,599,306 A * 2/1997 Klein et al.
5,928,181 A * 7/1999 Coleman et al. .............. 604/8

OTHER PUBLICATIONS

A. Pavie, PH. Leger, A. Nzomvuama, J. Szefner, M. Regan, E. Vaisser, and I. Gandjbakhch, "Left Centrifugal Pump Cardiac Assist with Transseptal Percutaneous Left Atrial Cannula", *Artifical Organs*, 22(6):502–507, Blackwell Science, Inc., 1998 International Society for Artifical Organs.

* cited by examiner

Primary Examiner—Brian L. Casler
Assistant Examiner—Catherine Serke
(74) Attorney, Agent, or Firm—Ansel M. Schwartz (57) ABSTRACT

A perfusion cannula for treating a patient. The, cannula includes a hollow tube adapted for insertion into a vessel of the patient and adapted for fluid flow. The tube has a proximal end. The tube has a primary hole disposed in proximity to the proximal end for release of fluid from the tube and at least a first perfusion hole disposed in the tube wall for release of fluid from the tube. The cannula includes a widener extending from the outer surface of the tube and effectively extending the outer diameter of the tube. The inner diameter of the tube is smooth and continuous and has a circular, cross-section throughout. The widener is in spaced relation from the proximal end and in proximity to and in operational relation with the first perfusion hole wherein fluid in able to escape from the first perfusion hole without obstruction by the vessel wall when the tube is in the vessel wall. A perfusion cannula for treating a patient having at least a first ridge. A system for treating a patient. A method for treating a patient.

28 Claims, 4 Drawing Sheets

FIG.1

PERFUSION CANNULA, METHOD AND SYSTEM

FIELD OF THE INVENTION

The present invention is related to a perfusion cannula which provides fluid to the lower extremities and toward the body. More specifically, t he present invention is related to a perfusion cannula which provides blood to the lower extremities and toward the body which utilizes ridges to form channels to allow blood to escape the cannula and reach a lower extremity.

BACKGROUND OF THE INVENTION

The use of a pump to supplement the action of the heart of a patient requires the introduction of oxygenated blood from the pump into the patient. This can occur by insertion of a cannula connected to the pump into the femoral artery. A cannula which only provides for introduction of blood in one direction towards the body of the patient creates a risk for the patient of loss of the patient's lower extremities, such as a leg, since little or no oxygenated blood will reach the leg. If the pump is utilized for long periods of time, this risk can become very great. U.S. Pat. No. 5,330,433, incorporated by reference herein, attempts to solve this problem. However, it requires a flash chamber to indicate if a diverting side hole is properly positioned in the artery.

The present invention provides for the use of a pump to assist the operation of the heart for pumping blood in the patient and provides blood to the body as well as the lower extremities of the patient. It is also easier to use than the cannula described in U.S. Pat. No. 5,330,433 since the present invention is essentially self-aligning in the vessel for perfusion holes of the cannula.

SUMMARY OF THE INVENTION

The present invention pertains to a perfusion cannula for treating a patient. The cannula comprises a hollow tube adapted for insertion into a vessel of the patient and adapted for fluid flow. The tube has a proximal end. The tube has a primary hole disposed in proximity to the proximal end for release of fluid from the tube and at least a first perfusion hole disposed in the tube wall for release of fluid from the tube. The cannula comprises a widener extending from the outer surface of the tube and effectively extending the outer diameter of the tube. The inner diameter of the tube is smooth and continuous and has a circular cross-section throughout. The widener is in spaced relation from the proximal end and in proximity to and in operational relation with the first perfusion hole wherein fluid is able to escape from the first perfusion hole without obstruction by the vessel wall when the tube is in the vessel wall.

The present invention pertains to a perfusion cannula for treating a patient. The cannula comprises a hollow tube adapted for insertion into a vessel of the patient and adapted for fluid flow. The tube has a proximal end. The tube has a primary hole disposed in proximity to the proximal end for release of fluid from the tube and at least a first perfusion hole disposed in the tube wall for release of fluid from the tube. The cannula comprises at least a first ridge disposed on the outer surface of the tube and effectively extending the outer diameter of the tube. The first ridge is in spaced relation from the proximal end and in proximity to and in operational relation with the first perfusion hole wherein fluid is able to escape from the first perfusion hole without obstruction by the vessel wall when the tube is in the vessel wall.

The present invention pertains to a system for treating a patient. The system comprises a perfusion cannula comprising a hollow tube adapted for insertion into a vessel of the patient and adapted for fluid flow. The tube has a proximal end. The tube has a primary hole disposed in proximity to the proximal end for release of fluid from the tube and a plurality of perfusion holes disposed in the tube wall for release of fluid from the tube. The tube has a plurality of ridges disposed on the outer surface of the tube and effectively extending the outer diameter of the tube. The ridges are in spaced relation from the proximal end and in proximity to and in operational relation with the plurality of perfusion holes which are disposed between the ridges wherein fluid is able to escape from the plurality of perfusion holes without obstruction by the vessel wall when the tube is in the vessel wall. The system comprises a pump mechanism for pumping fluid into the cannula. The pump mechanism is connected to the cannula.

The present invention pertains to a method for treating a patient. The method comprises the steps of inserting a tube through the skin of the patient into the femoral artery of the patient so ridges on the outside of the tube contact the inner wall of the femoral artery and create channels between the outer surface of the tube, the ridges and the inner surface of the femoral artery, and the inner surface of the femoral artery contacts the outer surface of the tube between the proximal end of the tube and the ridges on the tube. Then there is the step of pumping blood through the tube so the blood flows out a primary hole of the tube in proximity to the proximal end of the tube in a first direction in the artery and blood flows out perfusion holes in the wall of the tube between the ridges into the channels where the blood flows along the channels to a location where the inner surface of the artery makes contact with the outer surface of the tube and is directed back along the channels in a second direction in the vessel opposite the first direction.

The present invention pertains to a method for treating a patient. The method comprises the steps of inserting a tube into the femoral artery of the patient. Then there is the step of contacting the outer surface of the tube with the inner surface of the artery at a location. Next there is the step of forcing fluid into the tube so the fluid flows into the artery out a primary hole at the end of the tube in a first direction, and out perfusion holes in the tube into channels defined by the outer surface of the tube, ridges on the outer surface of the tube and the inner surface of the artery. Then there is the step of following fluid along the channels to the location. Next there is the step of diverting the fluid from the location in a second direction in the vessel opposite the first direction.

BRIEF DESCRIPTION OF THE DRAWINGS

In the accompanying drawings, the preferred embodiment of the invention and preferred methods of practicing the invention are illustrated in which.

DETAILED DESCRIPTION

Figure 1:
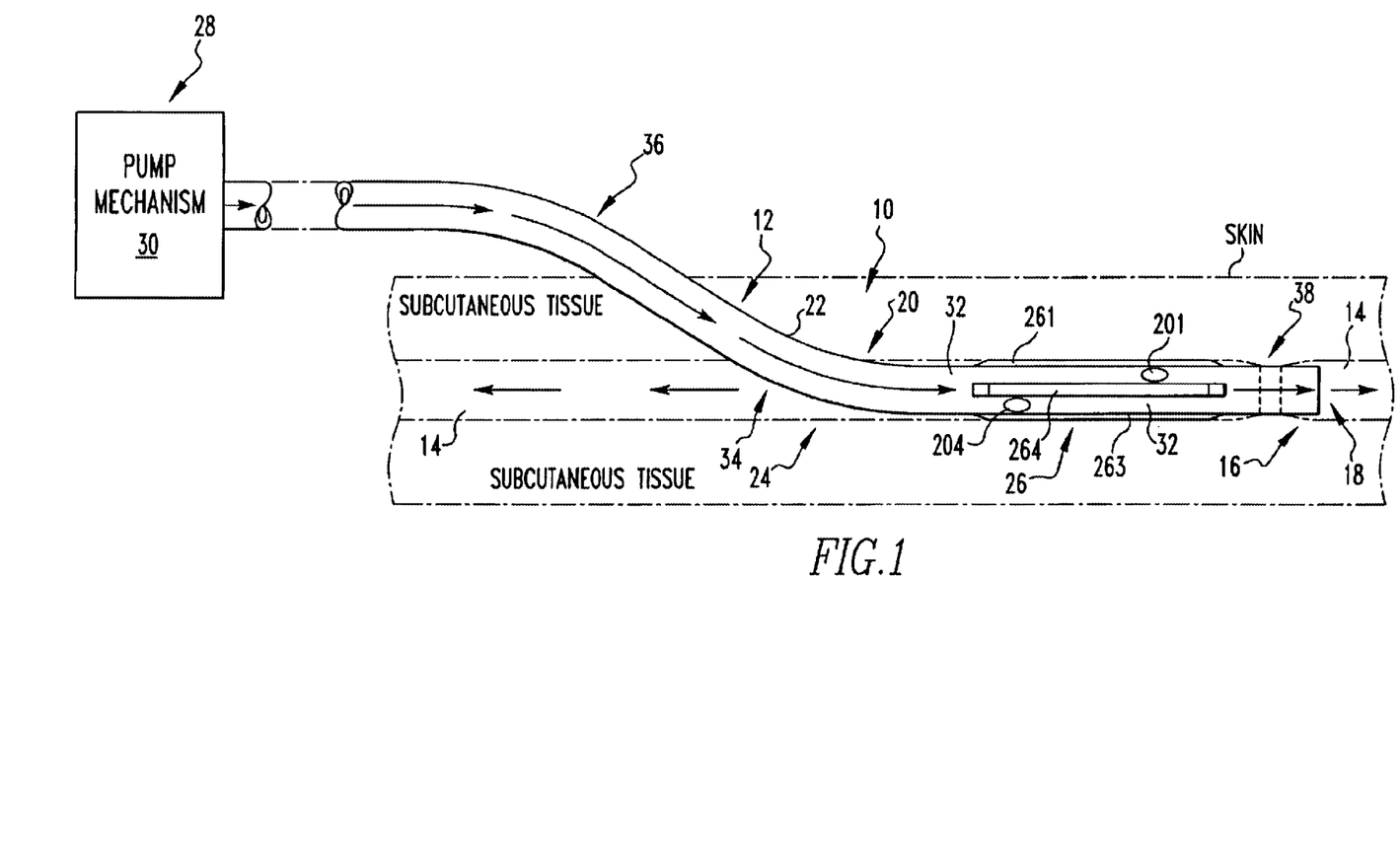
FIG. 1 is a schematic representation of a system of the present invention.
Figure 2A:
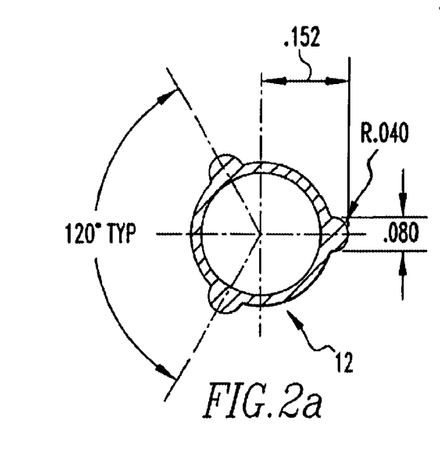
FIG. 2a is a schematic representation of section 2a of FIG. 2d.
Figure 2B:
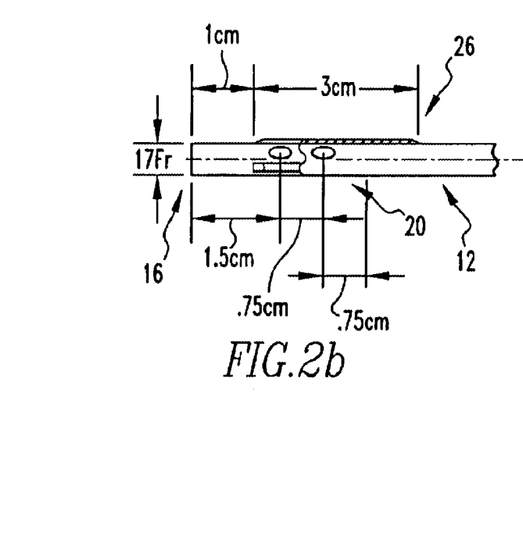
FIG. 2b is a schematic representation of section 2b of FIG. 2d.
Figure 2C:
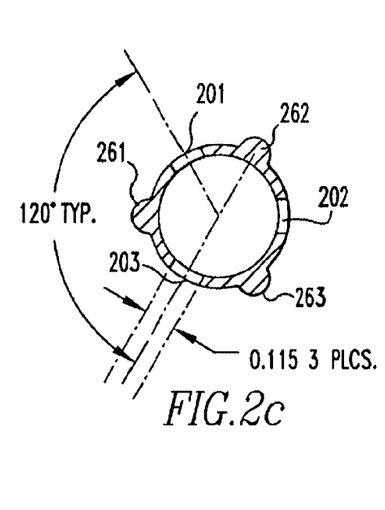
FIG. 2c is a schematic representation of section 2c of FIG. 2d.
Figure 2D:
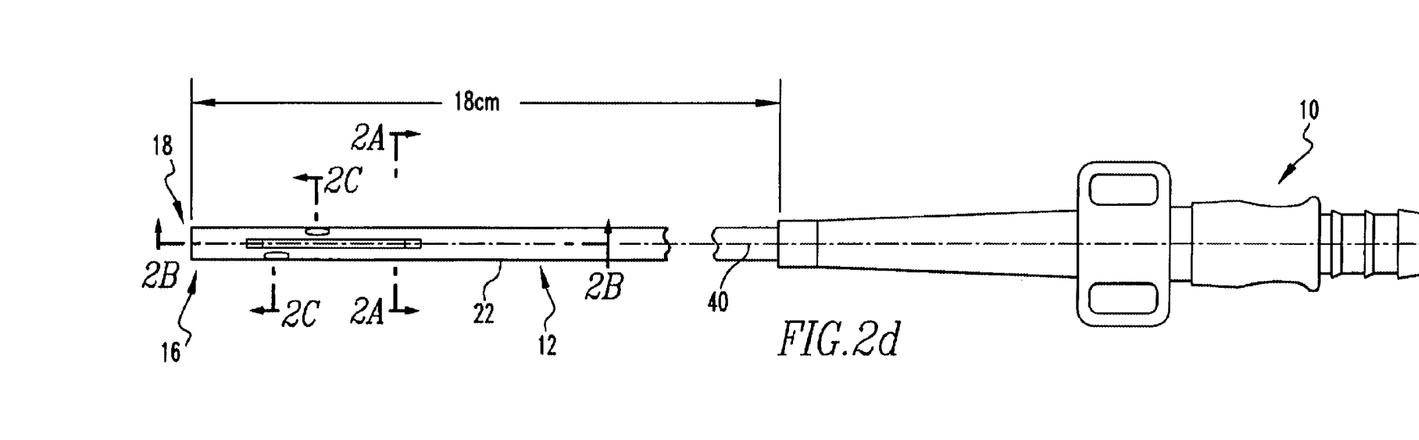
FIG. 2d is a schematic representation of a cannula having 3 ribs.

Referring now to the drawings wherein like reference numerals refer to similar or identical parts throughout the several views, and more specifically to FIG. 1 thereof, there is shown a perfusion cannula 10 for treating a patient. The cannula 10 comprises a hollow tube 12 adapted for insertion into a vessel, such as an artery 14, of the patient and adapted for fluid flow. The tube 12 has a proximal end 16. The tube 12 has a primary hole 18 disposed in proximity to the proximal end 16 for release of fluid from the tube 12 and at least a first perfusion hole 201 disposed in the tube wall 22 for release of fluid from the tube 12. The cannula 10 comprises a widener 24 extending from the outer surface of the tube 12 and effectively extending the outer diameter of the tube 12. The inner diameter of the tube 12 is smooth and continuous and has a circular cross-section throughout. The widener 24 is in spaced relation from the proximal end 16 and in proximity to and in operational relation with the first perfusion hole 201 wherein fluid is able to escape from the first perfusion hole 201 without obstruction by the inner wall of the vessel when the tube 12 is in the vessel wall. Preferably, the widener 24 and the tube 12 are one continuous piece.

The present invention pertains to a perfusion cannula 10 for treating a patient. The cannula 10 comprises a hollow tube 12 adapted for insertion into a vessel of the patient and adapted for fluid flow. The tube 12 has a proximal end 16. The tube 12 has a primary hole 18 disposed in proximity to the proximal end 16 for release of fluid from the tube 12 and at least a first perfusion hole 201 disposed in the tube wall 22 for release of fluid from the tube 12. The cannula 10 comprises at least a first ridge 261 disposed on the outer surface of the tube 12 and effectively extending the outer diameter of the tube 12. The first ridge 261 is in spaced relation from the proximal end 16 and in proximity to and in operational relation with the first perfusion hole 201 wherein fluid is able to escape from the first perfusion hole 201 without obstruction by the vessel wall when the tube 12 is in the vessel.

Preferably, the first ridge 261 and the tube 12 are one continuous piece. The tube 12 preferably has a ridge bend 34 in proximity to the first ridge 261. Preferably, the tube 12 has a distal bend 36 remote from the ridge bend 34 and from the proximal end 16. Alternatively, the tube 12 has no bends and is essentially straight.

The cannula 10 preferably includes a second ridge 262 and a third ridge 263, as shown in FIG. 2. The first ridge 261, second ridge 262 and third ridge 263 are preferably disposed equidistant from each other on the outer surface of the tube 12. Preferably, the cannula 10 includes a second perfusion hole 202 and a third perfusion hole 203 disposed in the tube wall 22 and between the first ridge 261 and second ridge 262, and between the second ridge 262 and third ridge 263, respectively.

Figure 3A:
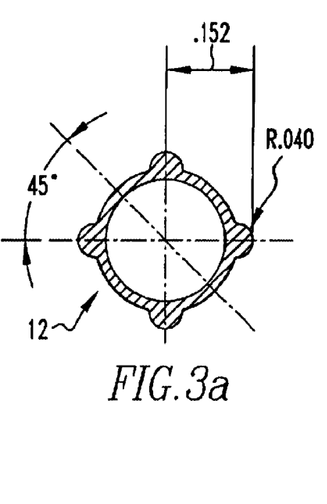
FIG. 3a is a schematic representation of section 3a of FIG. 3d.
Figure 3B:
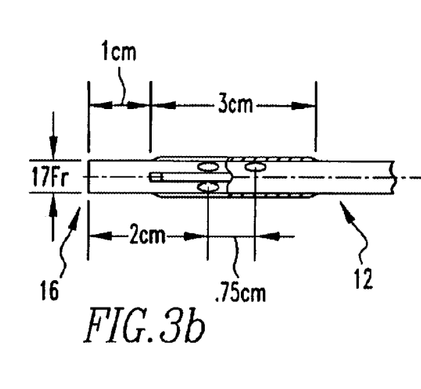
FIG. 3*b* is a schematic representation of section 3*b* of FIG. 3*d*.
Figure 3C:
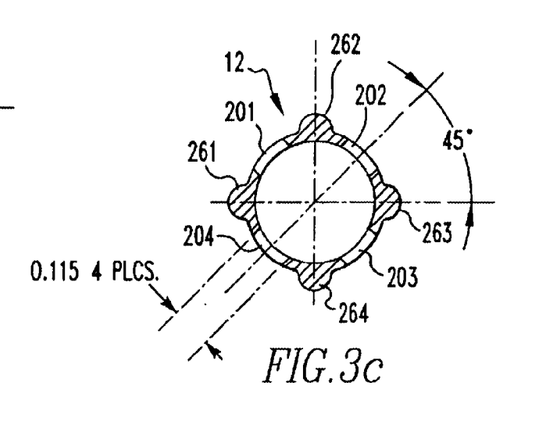
FIG. 3*c* is a schematic representation of section 3*c* of FIG. 3*d*.
Figure 3D:
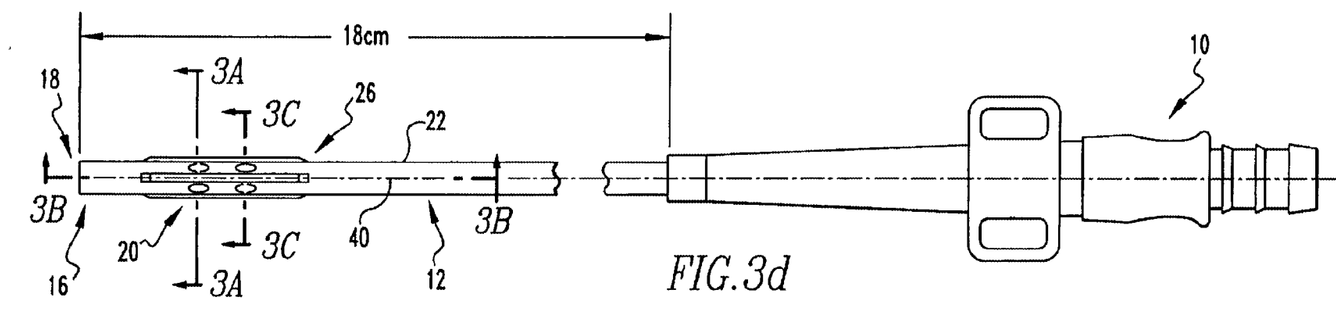
FIG. 3*d* is a schematic representation of a cannula having 4 ribs.

The cannula 10 preferably includes a fourth ridge 264, as shown in FIG. 2. The first ridge 261, second ridge 262, third ridge 263 and fourth ridge 264 are preferably disposed equidistant from each other on the outer surface of the tube 12. Preferably, the cannula 10 includes a fourth perfusion hole 204 disposed in the tube wall 22 and between the third ridge 263 and fourth ridge 264.

The tube 12 preferably has a longitudinal axis 40 and wherein the first ridge 261, second ridge 262, third ridge 263 and fourth ridge 264 are in parallel with each other and are in parallel with the longitudinal axis 40 of the tube 12. The second ridge 262, third ridge 263 and fourth ridge 264 are in spaced relation from the primary hole 18. Preferably, the first ridge 261 is at least one centimeter from the proximal end 16. The first ridge 261 is preferably approximately three centimeters long. The other ridges 26 and perfusion holes are similarly dimensioned.

The present invention pertains to a system 28 for treating a patient. The system 28 comprises a perfusion cannula 10 comprising a hollow tube 12 adapted for insertion into a vessel of the patient and adapted for fluid flow. The tube 12 has a proximal end 16. The tube 12 has a primary hole 18 disposed in proximity to the proximal end 16 for release of fluid from the tube 12 and a plurality of perfusion holes 20 disposed in the tube 12 wall for release of fluid from the tube 12. The tube 12 has a plurality of ridges 26 disposed on the outer surface of the tube 12 and effectively extending the outer diameter of the tube 12. The ridges 26 are in spaced relation from the proximal end 16 and in proximity to and in operational relation with the plurality of perfusion holes 20 which are disposed between the ridges 26 wherein fluid is able to escape from the plurality of perfusion holes 20 without obstruction by the vessel wall when the tube 12 is in the vessel wall. The system 28 comprises a pump mechanism 30 for pumping fluid into the cannula 10. The pump mechanism 30 is connected to the cannula 10.

The present invention pertains to a method for treating a patient. The method comprises the steps of inserting a tube 12 through the skin of the patient into the femoral artery 14 of the patient so ridges 26 on the outside of the tube 12 contact the inner wall of the femoral artery 14 and create channels 32 defined by the outer surface of the tube 12, the ridges 26 and the inner surface of the femoral artery 14, and the inner surface of the femoral artery 14 contacts the outer surface of the tube 12 between the proximal end 16 of the tube 12 and the ridges 26 on the tube 12 at a location 38. Then there is the step of pumping blood through the tube 12 so the blood flows out a primary hole 18 of the tube 12 in proximity to the proximal end 16 of the tube 12 in a first direction in the artery 14 and blood flows out perfusion holes 20 in the wall of the tube 12 between the ridges 26 into the channels 32 where the blood flows along the channels 32 to the location 38 where the inner surface of the artery 14 makes contact with the outer surface of the tube 12 and is directed from the location 38 back along the channels 32 in a second direction in the artery 14 opposite the first direction.

The present invention pertains to a method for treating a patient. The method comprises the steps of inserting a tube 12 into the femoral artery 14 of the patient. Then there is the step of contacting the outer surface of the tube 12 with the inner surface of the artery 14 at a location 38. Next there is the step of forcing fluid into the tube 12 so the fluid flows into the artery 14 out a primary hole 18 at the end of the tube 12 in a first direction, and out perfusion holes 20 in the tube 12 into channels 32 defined by the outer surface of the tube 12, ridges 26 on the outer surface of the tube 12 and the inner surface of the artery 14. Then there is the step of flowing fluid along the channels 32 to the location 38. Next there is the step of diverting the fluid from the location 38 in a second direction in the vessel opposite the first direction.

In the operation of the preferred embodiment, the cannula 10 connected to a pump mechanism 30 is inserted into the femoral artery of a patient so the proximal end 16 of the tube 12 of the cannula 10 is disposed in the femoral artery, as is well known in the art. The tube 12 has a ridge bend 34 that allows the tube 12 to extend in parallel with the artery 14 and then bend toward the surface of the skin of the patient and then bend again at a distal bend 36 so the tube 12 then extends essentially in parallel with the skin of the patient, to minimize it being bumped or knocked, to a connection point with the pump mechanism 30.

The tube 12 at its proximal end 16 has a primary hole 18 through which blood pumped from the pump mechanism 30 leaves the tube 12 and is directed toward the body of the patient. Spaced apart from the proximal end 16 of the tube 12 is a first ridge 261, a second ridge 262, a third ridge 263 and a fourth ridge 264 which are disposed equidistant from each other on the outside surface of the tube 12. The first ridge 261, second ridge 262, third ridge 263 and fourth ridge 264 are in parallel with each other and in parallel with the longitudinal axis 40 of the tube 12. The ridges 26 are formed during the extrusion process when the tube 12, made of plastic, is formed so that the ridges 26 and tube 12 are one continuous piece. The inner surface of the tube 12 is smooth and continuous and has essentially a constant inner diameter.

When the proximal end 16 of the tube 12 is properly positioned in the artery 14, the ridges 26 that extend from the outer surface of the tube 12 contact the inner wall of the artery 14 and effectively hold the inner wall of the artery 14 away from the outer surface of the tube 12. The space defined by the outer surface of the tube 12, the ridges 26 and the inner wall of the artery 14 pressing against the ridges 26 effectively forms channels 32. Between the first ridge 261 and second ridge 26 tube is a first perfusion hole 201 in the tube wall 22, between the second ridge 262 and the third ridge 263 is a second perfusion hole 202 in the tube wall 22, between the third ridge 263 and the fourth ridge 264 is a third perfusion hole 203 in the tube wall 22, and between the fourth ridge 264 and the first ridge 261 is a fourth perfusion hole 204 in the tube wall 22. From these perfusion holes 20 between the ridges 26 blood pumped from the pump mechanism 30 escapes from the tube 12 and flows into the respective channels to which the respective holes fluidically connect. The inner wall of the artery 14 does not obstruct the blood flow from the perfusion holes 20 since the ridges 26 effectively hold the inner wall of the artery 14 away from the outer surface of the tube 12 and thus from the perfusion holes 20 which are in the tube wall 22.

Between the proximal end 16 and the ridges 26 is only the outer surface of the tube 12, with nothing to hold the inner wall of the artery 14 away from this outer surface of the tube 12. Where the ridges 26 end, the inner wall of the artery 14 ideally contacts the outer surface of the tube 12 or presses against the tube 12, stopping blood which is flowing out of the perfusion holes 20 into the channels 32 from moving past the location 38 where the artery 14 contacts the tube 14, or slowing the blood flow due to the resistance of the artery pressing against the tube. Because the pressure of the blood escaping the perfusion holes 20 is greater than the pressure of the blood that is stopped by the artery contacting the tube 12, or slowed by the artery pressing against the tube, the blood is effectively diverted away from the location 38 and back along the respective channel 32 which the blood originally flowed along to reach the location 38, and passes the ridge bend 34 toward the lower extremity, such as the leg. This is simply because the pressure of the blood after it leaves the perfusion holes is not great enough to push through the location 38, or significantly overcome the resistence of the artery trying to close against the tube 12, and not of a great enough pressure to stop the blood from flowing out of the perfusion holes or to flow back into the perfusion holes, and thus has only one place to go, which is to the lower extremities of the patient by way of the femoral artery 14. Thus, the blood leaving the tube 12 through the primary hole 18 is headed in a first direction towards the body, while the blood which leaves the perfusion holes 20 is effectively diverted by the seal 38, heads in a second direction, opposite the first direction, towards the leg of the patient. This two-directional blood flow from the cannula 10 into the artery 14 provides blood toward all necessary parts of the patient so there is little risk that the leg of the patient could be compromise while the pump mechanism 30 is assisting the heart of the patient through the cannula 10.

The total flow rate from the cannula is between 2–5 L/min. and preferably 3–4 L/min. The flow rate from the perfusion holes 20 to the leg is between 100 cc/min. and 500 cc/min. and preferably 200 cc/min. and 400 cc/min.

Figure 4A:
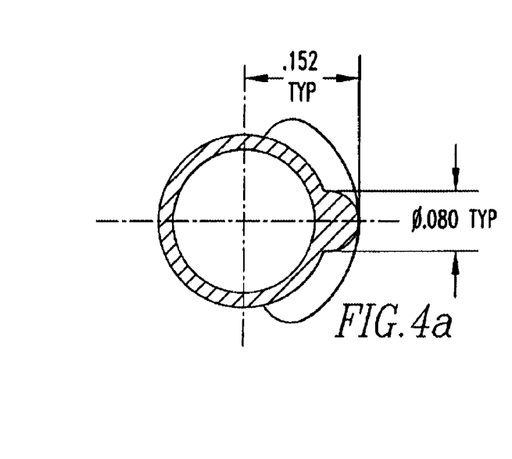
FIG. 4*a* is a schematic representation of section 4*a* of FIG. 4*c*.
Figure 4B:
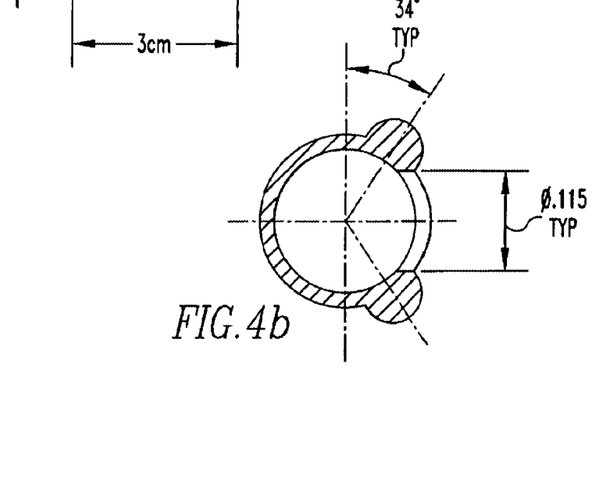
FIG. 4*b* is a schematic representation of section 4*b* of FIG. 4*c*.
Figure 4C:
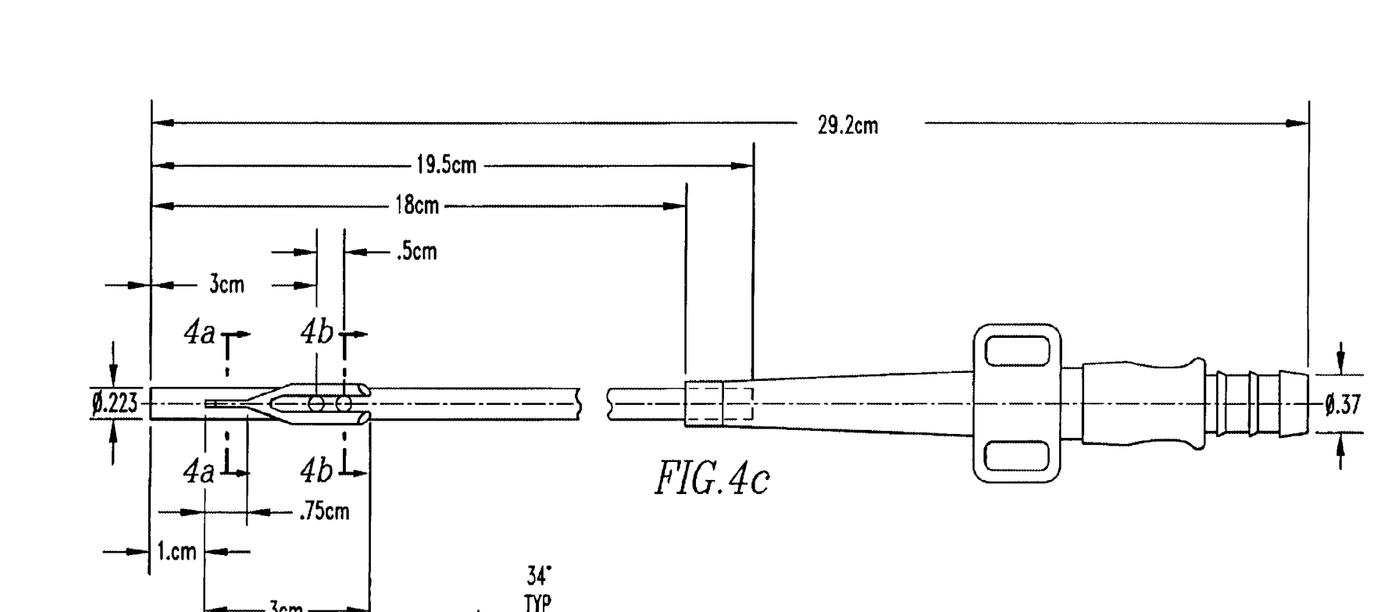
FIG. 4*c* is a schematic representation of a cannula having a bifurcated rib.

In another embodiment, as shown in FIGS. 4a–4c, a wishbone rib comprising 2 bifurcated ribs 201 extending from a lead rib 203 is disposed on the cannula. Two perfusion holes are disposed in the cannula between the bifurcated ribs 201. The bifurcated ribs serve to prevent the inner surface of the vessel from sealing the perfusion holes so blood cannot flow out of the perfusion holes.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. A system for treating a patient comprising:
   a perfusion cannula comprising:
      a hollow tube adapted for insertion into a vessel of the patient and adapted for fluid flow, said tube having a proximal end, said tube having a primary hole disposed in proximity to the proximal end for release of fluid from the tube and at least a first perfusion hole disposed in the tube wall for release of fluid from the tube, said tube having an outer diameter and an inner diameter; and
      a widener extending from the outer surface of the tube and effectively extending the outer diameter of the tube, said inner diameter of the tube smooth and continuous and having a circular cross-section throughout, said widener in spaced relation from the proximal end and in proximity to and in operational relation with the first perfusion hole and adopted for fluid to be able to escape from the first perfusion hole without obstruction by the vessel wall when the tube is in the vessel but allowing the vessel wall to close upon the tube between the first perfusion hole and the primary hole wherein fluid escaping from the first perfusion hole contacts the vessel wall about the tube and is stopped by the vessel wall from moving past the vessel wall and past the primary hole, said tube having a rigid bend in proximity to the widener; and
   a pump mechanism adapted for pumping fluid into the cannula and out of the first perfusion hole with enough pressure to travel in the vessel in a second direction through the leg of the patient, and out the primary hole with enough pressure to travel in the vessel in a first direction through the body of the patient when the cannula is inserted in the vessel, said pump mechanism connected to the cannula.

2. The cannula as described in claim 1 wherein the widener and the tube are one continuous piece.

3. The system as described in claim 1 wherein the pump mechanism pumps fluid from the cannula at a total flow rate between 2–5 L/min and fluid from the perfusion holes at a flow rate between 100 cc/min and 500 cc/min.

4. A system for treating a patient comprising:
   a perfusion cannula comprising:
      a hollow tube adapted for insertion into a vessel of the patient and adapted for fluid flow, said tube having a proximal end, said tube having a primary hole disposed in proximity to the proximal end for release of fluid from the tube and at least a first perfusion hole disposed in the tube wall for release of fluid from the tube; and
      at least a first ridge disposed on the outer surface of the tube and effectively extending the outer diameter of the tube, said first ridge in spaced relation from the primary hole of the proximal end and in proximity to and in operational relation with the first perfusion hole and adapted for wherein fluid to be able to escape from the first perfusion hole without obstruction by the vessel wall when the tube is in the vessel but allowing the vessel wall to close upon the tube between the first perfusion hole and the primary hole wherein fluid escaping from the first perfusion hole contacts the vessel wall about the tube and is stopped by the vessel wall from moving past the vessel wall and past the primary hole, the tube has a rigid bend in proximity to the first ridge; and
      a pump mechanism adapted for pumping fluid into the cannula and out of the first perfusion hole with enough pressure to travel in the vessel in a second direction through the leg of the patient, and out the primary hole with enough pressure to travel in the vessel in a first direction through the body of the patient when the cannula is inserted in the vessel, said pump mechanism connected to the cannula.

5. The system as described in claim 4 wherein the pump mechanism pumps fluid from the cannula at a total flow rate between 2–5 L/min and fluid from the perfusion holes at a flow rate between 100 cc/min and 500 cc/min.

6. The cannula as described in claim 5 wherein the first ridge and the tube are one continuous piece.

7. A cannula as described in claim 6 wherein the tube has a distal bend remote from the ridge bend and from the proximal end.

8. The cannula as described in claim 6 including a second ridge and a third ridge; said first ridge, second ridge and third ridge disposed equidistant from each other on the outer surface of the tube.

9. The cannula as described in claim 8 including a second perfusion hole and a third perfusion hole disposed in the tube wall and between the first ridge and second ridge, and between the second ridge and third ridge, respectively.

10. The cannula as described in claim 9 including a fourth ridge; said first ridge, second ridge, third ridge and fourth ridge disposed equidistant from each other on the outer surface of the tube.

11. The cannula as described in claim 10 including a fourth perfusion hole disposed in the tube wall and between the third ridge and fourth ridge.

12. The cannula as described in claim 11 wherein the tube has a longitudinal axis and wherein the first ridge, second ridge, third ridge and fourth ridge are in parallel with each other and are in parallel with the longitudinal axis of the tube; said second ridge, third ridge and fourth ridge in spaced relation from the primary hole.

13. The cannula as described in claim 12 wherein the first ridge is at least one centimeter from the proximal end.

14. The cannula as described in claim 13 wherein the first ridge is approximately three centimeters long.

15. A system for treating a patient comprising:
   a perfusion cannula comprising a hollow tube adapted for insertion into a vessel of the patient and adapted for fluid flow, said tube having a proximal end, said tube having a primary hole disposed in proximity to the proximal end for release of fluid from the tube and a plurality of perfusion holes disposed in the tube wall for release of fluid from the tube; and a plurality of ridges disposed on the outer surface of the tube and effectively extending the outer diameter of the tube, the ridges in spaced relation from the proximal end and in proximity to and in operational relation with the plurality of perfusion holes which are disposed between the ridges wherein fluid is able to escape from the plurality of perfusion holes without obstruction by the vessel wall when the tube is in the vessel, the tube has a rigid bend in proximity to the ridges; and
   a pump mechanism for pumping fluid into the cannula, said pump mechanism connected to the cannula.

16. The system as described in claim 15 wherein the pump mechanism pumps fluid from the cannula at a total flow rate between 2–5 L/min and fluid from the perfusion holes at a flow rate between 100 cc/min and 500 cc/min.

17. A method for treating a patient comprising the steps of:
   inserting a tube through the skin of the patient into the femoral artery of the patient so ridges on the outside of the tube contact the inner wall of the femoral artery and create channels between the outer surface of the tube, the ridges and the inner surface of the femoral artery, and the inner surface of the femoral artery contacts the outer surface of the tube between a proximal end of the tube and the ridges on the tube;
   maintaining the tube in the femoral artery; and
   pumping blood with a pump through the tube while the tube is maintained in the femoral artery so the blood flows with enough pressure out a primary hole of the tube in proximity to the proximal end of the tube in a first direction toward the body in the artery and blood flows with enough pressure out perfusion holes in the wall of the tube between the ridges into the channels where blood flows along the channels to a location where the inner surface of the artery makes contact with the outer surface of the tube and is directed back along the channels in a second direction in the artery to the leg opposite the first direction.

18. The method as described in claim 17 wherein the pumping step includes the step of pumping fluid from the tube at a total flow rate between 2–5 L/min and fluid from the perfusion holes at a flow rate between 100 cc/min and 500 cc/min.

19. A method for treating a patient comprising the steps of:
   inserting a tube into the femoral artery of the patient;
   contacting the outer surface of the tube with the inner surface of the artery at a location;

maintaining the tube in the femoral artery;

forcing fluid into the tube with a pump while the tube is maintained in the femoral artery so the fluid flows into the artery out a primary hole at a proximal end of the tube in a first direction with enough pressure to flow through the body of the patient, and out perfusion holes in the tube into channels defined by the outer surface of the tube, ridges on the outer surface of the tube and the inner surface of the artery with enough pressure to flow through the leg of the patient;

following fluid along the channels to the location; and diverting the fluid from the location in a second direction in the artery toward the leg opposite the first direction toward the body.

20. The method as described in claim 19 wherein the forcing step includes the step of forcing fluid from the tube at a total flow rate between 2–5 L/min and fluid from the perfusion holes at a flow rate between 100 cc/min and 500 cc/min.

21. A system for treating a patient comprising:
a perfusion cannula comprising:
   a hollow tube adapted for insertion into a vessel of the patient and adapted for fluid flow, said tube having a proximal end, said tube having a primary hole disposed in proximity to the proximal end for release of fluid from the tube and at least a first perfusion hole disposed in the tube wall for release of fluid from the tube, said tube having an outer diameter and an inner diameter; and
   a widener extending from the outer surface of the tube and effectively extending the outer diameter of the tube, said inner diameter of the tube smooth and continuous and having a circular cross-section throughout, said widener in spaced relation from the proximal end and in proximity to and in operational relation with the first perfusion hole and adopted for fluid to be able to escape from the first perfusion hole without obstruction by the vessel wall when the tube is in the vessel but allowing the vessel wall to close upon the tube between the first perfusion hole and the primary hole wherein fluid escaping from the first perfusion hole contacts the vessel wall about the tube and is stopped by the vessel wall from moving past the vessel wall and past the primary hole; and
   a pump mechanism adapted for pumping fluid into the cannula and out of the first perfusion hole with enough pressure to travel in the vessel in a second direction through the leg of the patient, and out the primary hole with enough pressure to travel in the vessel in a first direction through the body of the patient when the cannula is inserted in the vessel, the pump mechanism pumps fluid from the cannula at a total flow rate between 2–5 L/min and fluid from the first perfusion hole at a flow rate between 100 cc/min and 500 cc/min, said pump mechanism connected to the cannula.

22. A system for treating a patient comprising:
a perfusion cannula comprising:
   a hollow tube adapted for insertion into a vessel of the patient and adapted for fluid flow, said tube having a proximal end, said tube having a primary hole disposed in proximity to the proximal end for release of fluid from the tube and at least a first perfusion hole disposed in the tube wall for release of fluid from the tube; and
   at least a first ridge disposed on the outer surface of the tube and effectively extending the outer diameter of the tube, said first ridge in spaced relation from the primary hole of the proximal end and in proximity to and in operational relation with the first perfusion hole and adapted for wherein fluid to be able to escape from the first perfusion hole without obstruction by the vessel wall when the tube is in the vessel but allowing the vessel wall to close upon the tube between the first perfusion hole and the primary hole wherein fluid escaping from the first perfusion hole contacts the vessel wall about the tube and is stopped by the vessel wall from moving past the vessel wall and past the primary hole; and
   a pump mechanism adapted for pumping fluid into the cannula and out of the first perfusion hole with enough pressure to travel in the vessel in a second direction through the leg of the patient, and out the primary hole with enough pressure to travel in the vessel in a first direction through the body of the patient when the cannula is inserted in the vessel, the pump mechanism pumps fluid from the cannula at a total flow rate between 2–5 L/min and fluid from the first perfusion hole at a flow rate between 100 cc/min and 500 cc/min, said pump mechanism connected to the cannula.

23. A method for treating a patient comprising the steps of:
inserting a tube through the skin of the patient into the femoral artery of the patient so ridges on the outside of the tube contact the inner wall of the femoral artery and create channels between the outer surface of the tube, the ridges and the inner surface of the femoral artery, and the inner surface of the femoral artery contacts the outer surface of the tube between a proximal end of the tube and the ridges on the tube; and
pumping blood with a pump through the tube at a total flow rate between 2–5 L/min so the blood flows with enough pressure out a primary hole of the tube in proximity to the proximal end of the tube in a first direction toward the body in the artery and blood flows at a flow rate between 100 cc/min and 500 cc/min with enough pressure out perfusion holes in the wall of the tube between the ridges into the channels where blood flows along the channels to a location where the inner surface of the artery makes contact with the outer surface of the tube and is directed back along the channels in a second direction in the artery to the leg opposite the first direction.

24. A method for treating a patient comprising the steps of:
inserting a tube into the femoral artery of the patient;
contacting the outer surface of the tube with the inner surface of the artery at a location;
forcing fluid into the tube with a pump so the fluid flows at a total flow rate between 2–5 L/min into the artery out a primary hole at a proximal end of the tube in a first direction with enough pressure to flow through the body of the patient, and out perfusion holes at a flow rate between 100 cc/min and 500 cc/min in the tube into channels defined by the outer surface of the tube, ridges on the outer surface of the tube and the inner surface of the artery with enough pressure to flow through the leg of the patient;
following fluid along the channels to the location; and
diverting the fluid from the location in a second direction in the artery toward the leg opposite the first direction toward the body.

25. A system for treating a patient comprising:

a perfusion cannula comprising a hollow tube adapted for insertion into a vessel of the patient and adapted for fluid flow, said tube having a proximal end, said tube having a primary hole disposed in proximity to the proximal end for release of fluid from the tube and a plurality of perfusion holes disposed in the tube wall for release of fluid from the tube; and a plurality of ridges disposed on the outer surface of the tube and effectively extending the outer diameter of the tube, the ridges in spaced relation from the proximal end and in proximity to and in operational relation with the plurality of perfusion holes which are disposed between the ridges wherein fluid is able to escape from the plurality of perfusion holes without obstruction by the vessel wall when the tube is in the vessel; and a pump mechanism for pumping fluid into the cannula, the pump mechanism pumps fluid from the cannula at a total flow rate between 2–5 L/min and fluid from the perfusion holes at a flow rate between 100 cc/min and 500 cc/min, said pump mechanism connected to the cannula.

26. A system for treating a patient comprising:

a perfusion cannula comprising a hollow tube adapted for insertion into a vessel of the patient and adapted for fluid flow, said tube having a proximal end, said tube having a primary hole disposed in proximity to the proximal end for release of fluid from the tube and a plurality of perfusion holes disposed in the tube wall for release of fluid from the tube, said tube having an outer diameter and an inner diameter; and a pump mechanism adapted for pumping fluid into the cannula and out of the plurality of perfusion holes with enough pressure to travel in the vessel in a second direction through the leg of the patient, and out the primary hole with enough pressure to travel in the vessel in a first direction through the body of the patient when the cannula is inserted in the vessel, the pump mechanism pumps fluid from the cannula at a total flow rate between 2–5 L/min and fluid from the perfusion holes at a flow rate between 100 cc/min and 500 cc/min, said pump mechanism connected to the cannula.

27. A system as described in claim 26 wherein the perfusion cannula includes a widener extending from the outer surface of the tube and effectively extending the outer diameter of the tube, said inner diameter of the tube. smooth and continuous and having a circular cross-section throughout, said widener in spaced relation from the proximal end and in proximity to and in operational relation with the perfusion holes and adopted for fluid to be able to escape from the perfusion holes without obstruction by the vessel wall when the tube is in the vessel but allowing the vessel wall to close upon the tube between the perfusion holes and the primary hole wherein fluid escaping from the perfusion holes contacts the vessel wall about the tube and is stopped by the vessel wall from moving past the vessel wall and past the primary hole.

28. A method for treating a patient comprising the steps of:

inserting a tube through the skin of the patient into the femoral artery of the patient; and pumping blood with a pump through the tube at a total flow rate between 2–5 L/min so the blood flows with enough pressure out a primary hole of the tube in proximity to the proximal end of the tube in a first direction toward the body in the artery and blood flows at a flow rate between 100 cc/min and 500 cc/min with enough pressure out perfusion holes in the wall of the tube and is directed in a second direction in the artery to the leg opposite the first direction.

* * * * *